United States Patent
Hu et al.

(10) Patent No.: US 6,842,532 B2
(45) Date of Patent: Jan. 11, 2005

(54) THREE DIMENSIONAL MEASUREMENT, EVALUATION AND GRADING SYSTEM FOR FABRIC/TEXTILE STRUCTURE/GARMENT APPEARANCE

(75) Inventors: Jinlian Hu, Kowloon (HK); Binjie Xin, Kowloon (HK)

(73) Assignee: The Hong Kong Polytechnic University, Kowloon (HK)

(*) Notice: Subject to any disclaimer, the term of this patent is extended or adjusted under 35 U.S.C. 154(b) by 562 days.

(21) Appl. No.: 09/778,857

(22) Filed: Feb. 8, 2001

(65) Prior Publication Data

US 2002/0146153 A1 Oct. 10, 2002

(51) Int. Cl.[7] .................................................. G06K 9/00
(52) U.S. Cl. ..................... 382/111; 345/582; 356/238.1; 700/144
(58) Field of Search ................................ 382/111, 141, 382/143, 154, 168, 169, 170, 181, 193, 201, 203, 318; 345/581, 582, 583, 585, 588, 630, 631; 356/238.1, 238.2, 238.3; 348/370, 168, 164, 372; 385/12, 37, 130, 131; 700/130, 144; 703/6

(56) References Cited

U.S. PATENT DOCUMENTS

| | | | | |
|---|---|---|---|---|
| 4,715,718 A | * | 12/1987 | Evans | ........................ 356/446 |
| 4,904,877 A | * | 2/1990 | Pietzsch | ................. 250/559.49 |
| 4,941,183 A | * | 7/1990 | Bruder et al. | ................ 382/111 |
| 5,125,034 A | * | 6/1992 | Hudson et al. | ............. 382/111 |
| 5,204,913 A | * | 4/1993 | Morooka et al. | ........... 382/111 |
| 5,255,352 A | * | 10/1993 | Falk | ........................... 345/582 |
| 5,533,145 A | * | 7/1996 | Shofner et al. | ............. 382/141 |
| 5,680,333 A | * | 10/1997 | Jansson | ......................... 703/6 |
| 5,739,904 A | * | 4/1998 | Berger et al. | ............ 356/238.2 |
| 5,751,834 A | * | 5/1998 | Lisk, Jr. | ..................... 382/111 |
| 5,753,931 A | * | 5/1998 | Borchers et al. | ........ 250/559.22 |
| 6,310,627 B1 | * | 10/2001 | Sakaguchi | .................. 345/630 |

* cited by examiner

Primary Examiner—Bhavesh M. Mehta
Assistant Examiner—Seyed Azarian
(74) Attorney, Agent, or Firm—Leydig, Voit & Mayer, Ltd.

(57) ABSTRACT

A method of three dimensional measurement, evaluation, and grading system for fabric/textile structure/garment appearance, based an values P and Q, is carried out using a fixed digital camera positioned above a piece of the fabric, shining at least two different parallel light beams from inclined directions onto the surface of the fabric and capturing different reflected images of the surface with the camera. The captured images are analysed to derive certain parameters relevant to the appearance. In particular, values of P+Q may be used in a grading evaluation, where P and Q are summations of the surface gradients for a plurality of evenly distributed points in an x direction and in a y direction of the surface, respectively.

8 Claims, 5 Drawing Sheets

Surface Model and Observation System

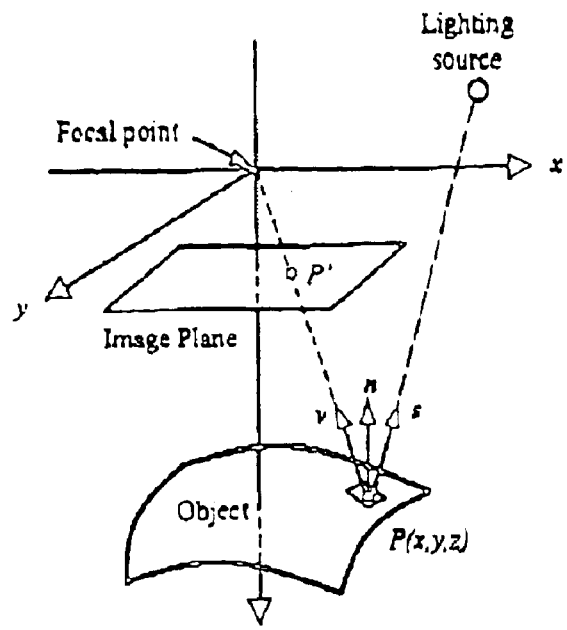
Figure 1 Surface Model and Observation System
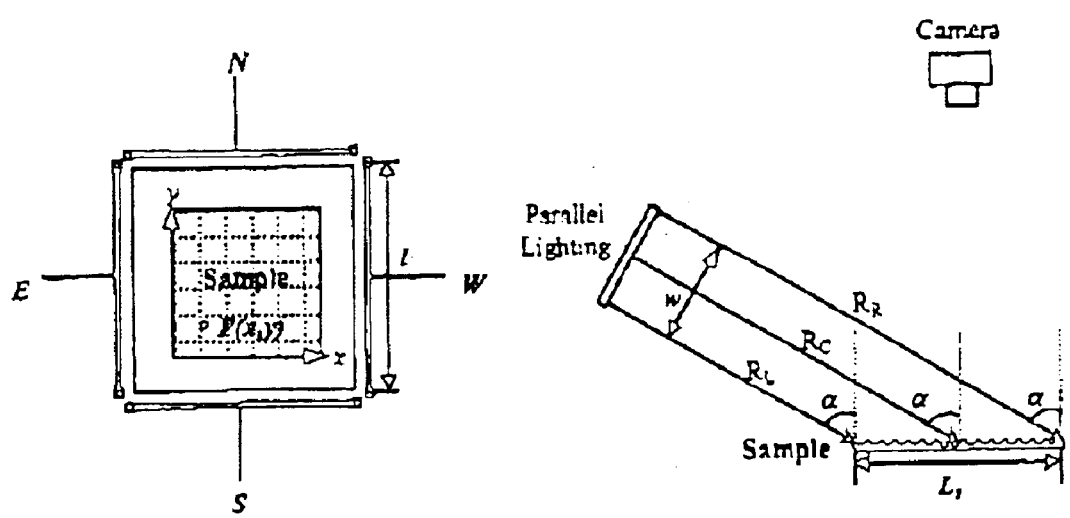
Figure 2 Lighting System

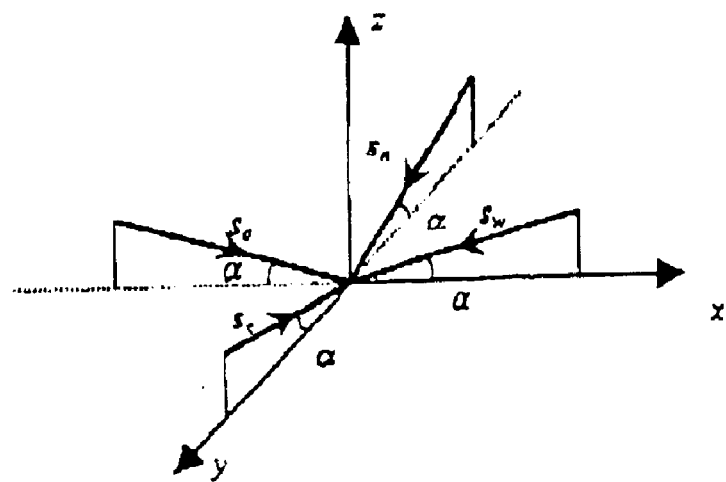
Fig.3 Four direction lighting vectors
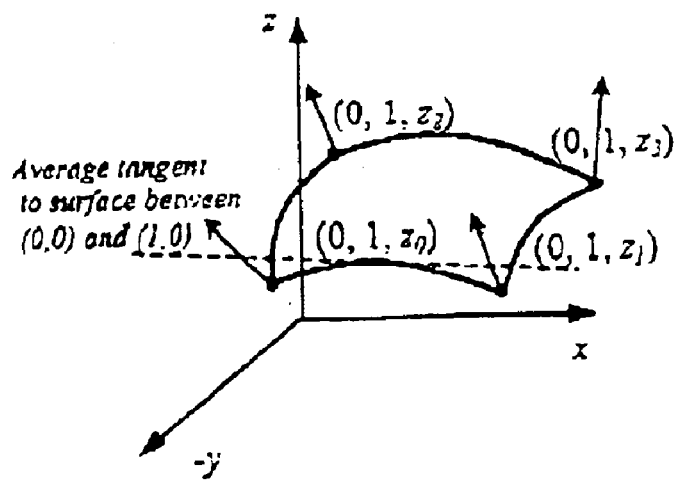
Fig.4 Surface patch and normal vectors
Approximation to surface between points (0,0) and (1,0) can be made by using the average tangent line if points are sufficiently close.

```
  o  o 2 •  o  o        3  2  o  •2 •3
                        •  •      
  o  o 1 •  o  o        2  1  o  •1 •2
                        •  •      
  2  1  •  1  2         o  o  o  o  o
  •  •     •  • o  o 1 •  o  o        •2 •1 o  •1 •2 o  o 2 •  o  o        •  •  o  •  •
                        3  2     2  3
```

(a)                    (b)

Figure 5 Illustration of depth conversion order for points on the object's surface.
(a) Initially, z values along the axes are calculated which is illustrated numerically.
(b) After z values are established along the axes, z values are computed for points in each quadrant in column major order as illustrated.

  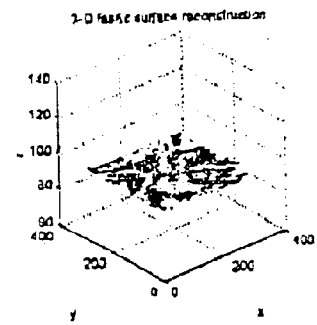

(a) Camera Acquired Fabric Image   (b) Revealed Surface Image   (c) 3-D Image of Fabric Figure 6 Fabric Surface Reconstruction

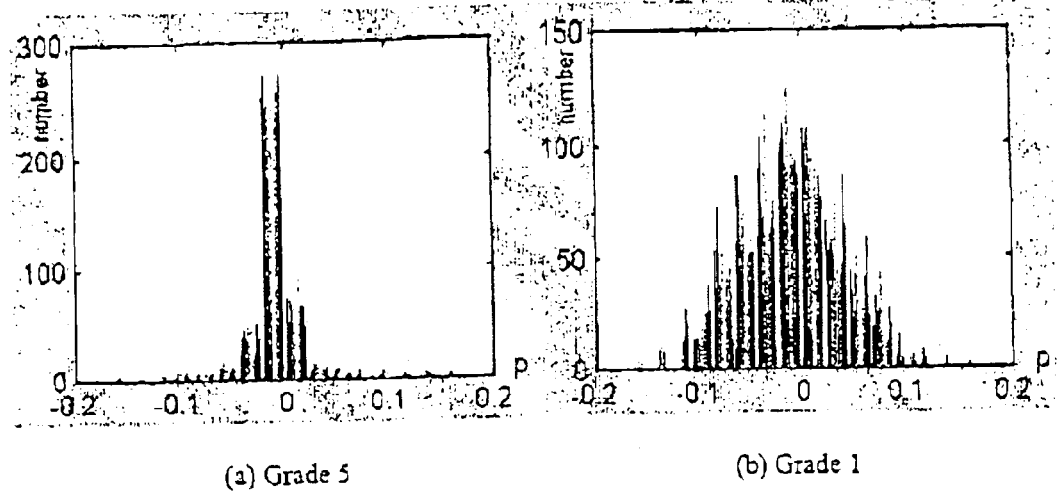
(a) Grade 5  (b) Grade 1
Figure 7 Distribution of $p$
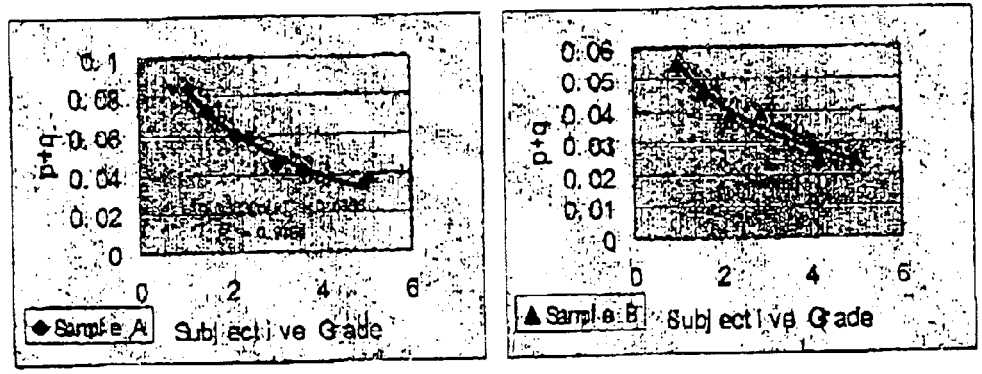
Figure 8

THREE DIMENSIONAL MEASUREMENT, EVALUATION AND GRADING SYSTEM FOR FABRIC/TEXTILE STRUCTURE/GARMENT APPEARANCE

BACKGROUND OF THE INVENTION

1. Field of the Invention

The invention relates to measuring, evaluating and grading fabric/textile structure/garment appearance.

2. Description of Prior Art

Fabric/garment/textile structure appearance includes many aspects such as pilling, wrinkling, seam puckering, and so forth. Although the invention applies to different aspects of fabric/textile structure/garment appearance, we explain below the effect of wrinkling on appearance. Wrinkles are three dimensional versions of creases, and form when fabrics are forced to develop high levels of double curvature, which result in some degree of permanent in-plane and out-of-plane deformations. Due to the importance of wrinkle recovery in the appearance of garments or textiles, many methods of assessment have been developed since the early 1950s. One of the most widely used in U.S. is the AATCC Test method. This method allows expert observers to compare fabric specimens with a set of six three-dimensional replicas supplied by the American Association of Textile Chemists and Colorists (AATCC), and then assign a grade according to their similarity.

Many attempts have been mode to automate this characterization process using imaging technology instead of visual observations. Laser probing is one way of evaluation of a fabric specimen to measure surface height variations. It incorporates obvious physical meaning and is not influenced by color and pattern in the specimen. However, point-scanning and costs make the method too slow and too expensive for industrial applications. A video camera with a common lighting system can be used to obtain good resolution images of fabric specimens and is faster than using a laser probe, but it is sensitive to fabric colors and patterns, so its application is also limited by its ability to evaluate only fabrics without patterns or designs. A line laser profilometer can be used to improve the detecting efficiency, but line profiles cannot cover a whole fabric surface, and typically sixteen images per sample are needed to produce reliable results

SUMMARY OF THE INVENTION

It is an object of the invention to obtain 3-D surface information more quickly and easily.

According to one aspect of the present invention there is provided a method of 3D measurement, evaluation and grading system for fabric/textile structure/garment appearance, the method comprising using a fixed digital camera positioned above a piece of the fabric, shining at least two different parallel light beams from inclined directions on to the surface and capturing different reflected images of the surface with the camera, analysing the captured images to derive values parameters of the surface based on intensities of light reflected from a number of evenly distributed points of the surface.

The method preferably includes using four different evenly distributed parallel light beams.

According to another aspect of the invention the there is provided an apparatus for 3D measurement, evaluation and grading system for fabric/textile structure/garment appearance, the apparatus including a digital camera arranged to be mounted above a piece of fabric, means to shine at least two inclined different parallel beams onto a surface of the fabric below the camera, means for analysing images of the fabric captured by the camera, and a computer programmed to derive values of P and Q from the captured images, where P and Q are summations of surface gradients for a plurality of evenly distributed points in an x direction and in a y direction respectively.

The invention may provide a method of grading fabric/textile structure appearance based on values P and Q, the method comprises using a fixed digital camera positioned above a piece of the fabric, shining at least two different parallel light beams from inclined directions on to the surface and capturing different reflected images of the surface with the camera, analysing the captured images to derive values of P and Q, where P and Q are summations of surface gradients for a plurality of evenly distributed points in an x direction and in a y direction respectively, and calibrating P+Q against a subjective grade analysis of the fabric, and thereafter using calibrated P and Q to determine the grades of fabric.

The method of grading preferably includes using four different parallel light beams.

The apparatus may comprise a digital camera arranged to be mounted above a piece of fabric, means to separately shine at least two inclined different parallel beams onto a surface of the fabric below the camera, means for analysing separate images of the fabric captured by the camera for each light beam respectively, and a computer programmed to derive of values parameters of the surface based on the intensities of light reflected from a number of evenly distributed points of the surface.

BRIEF DESCRIPTION OF THE DRAWINGS

A method and apparatus measuring wrinkling according to the invention will now be described by way of example with reference to the accompanying drawings in which:

FIG. 1 shows a surface model and observation system;

FIG. 2 shows a lighting system;

FIG. 3 shows a lighting vector diagram;

FIG. 4 shows a vector diagram for generating a shape of a surface of a patch;

FIGS. 5(a) and 5(b) are illustrations of depth conversion order for points on a specimen surface;

FIG. 6 shows images of a pieces of fabric;

FIG. 7 is a distribution graph of values of a region of a fabric;

FIG. 8 are graphs showing correlations between derived coefficients and subjective wrinkling grades.

DESCRIPTION OF THE PREFERRED EMBODIMENTS

Figure 9:
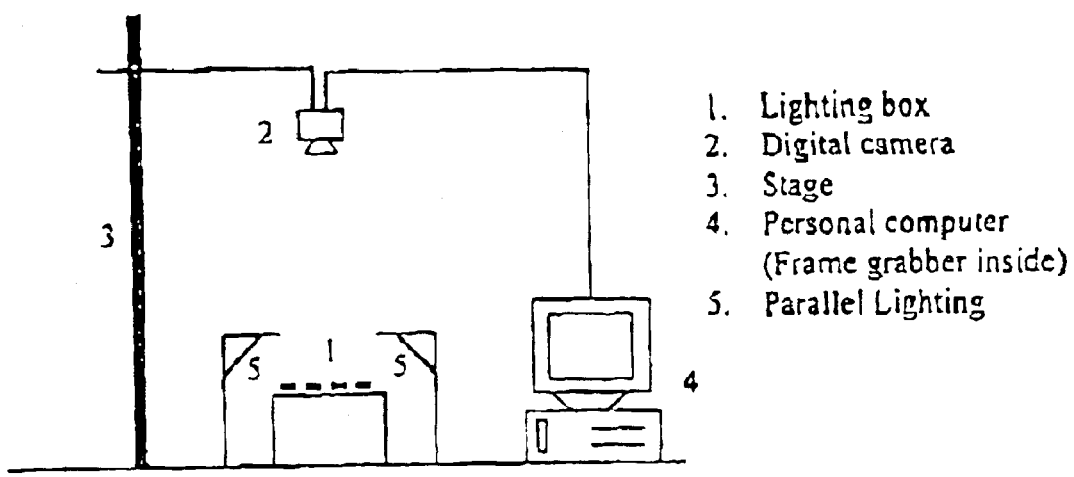
FIG. 9 shows the physical layout of an image capturing apparatus.

Referring to the drawings, the method relies on shining four parallel light sources on to a surface of a fabric specimen. When a ray of light strikes the surface of fabric, specular and diffuse reflections take place. These reflection characteristics depend on the surface of the material, surface microstructure, incident wavelength, and the direction of incidence of the light. However, it is acceptable to visualize most fabric surfaces as Lambertian surfaces, which scatter incident light equally in all directions and appear equally bright from all directions (see FIG. 1).

According to Lambert's cosine law, the intensity of an image element P' corresponding to a Lambertian reflecting surface is given by the relationship $$I(x,y) = c(x,y) \cos \theta \quad (1)$$

Where c(x,y) is the reflective parameter of corresponding surface element P, and θ is the incident angle at this element. As shown in FIG. 1, P,n,s,v are respectively a surface element of an object, normal vector of P, vector of P, incident vector of P, and vector of sight of P. cosθ is expressed by Eqn.2.

$$\cos\theta = n \cdot s \qquad (2)$$

It is easily understood that this is not constant for colored or patterned fabric surfaces, different color surfaces propose different c(x,y), although it can be considered as a constant parameter for solid fabrics. So the influence of color and pattern can be eliminated if c(x,y) can be calculated.

In the lighting system in FIG. 2, four evenly distributed parallel light sources with the same radiance intensity $E_0$ are used as incident light, and they are designed to illuminate fabric specimens from four different directions, i.e. east, west, south and north as shown in the Figure. The length and width of each of them are l and w respectively, α is the illuminating angle (zenith angle) of the four parallel light sources, $R_l$, $R_m$, $R_r$ are the distances between light source and left, middle, right parts of fabric sample surface respectively. According to photometry theory, irradiance of one surface element P(x,y) can be expressed by Eqn. 3.

$$E(x, y) = \frac{E \cos\alpha}{R^2(x, y)} \qquad (3)$$

Here, R(x,y) is the distance between the light source and the surface element P and it can be calculated from x,y.

When p and q are the first partial derivatives of z with respect to x and y, the normal vector of a surface element is given by Eqn.4.

$$n = \frac{(p, q, -1)}{\sqrt{p^2 + q^2 + 1}} \qquad (4)$$

In the observing system, east lighting vector $S_e = [\operatorname{ctg}\alpha\ 0\ -1]$; west lighting vector $S_w = [-\operatorname{ctg}\alpha\ 0\ -1]$; south lighting vector $S_s = [0\ -\operatorname{ctg}\alpha\ -1]$; north lighting, vector $S_n = [0\ \operatorname{ctg}\alpha\ -1]$; are shown in FIG. 3.

$$\begin{cases} I_e(x, y) = E_e(x, y) \cdot c(x, y) \cdot \cos\theta_e \\ I_w(x, y) = E_w(x, y) \cdot c(x, y) \cdot \cos\theta_w \\ I_s(x, y) = E_s(x, y) \cdot c(x, y) \cdot \cos\theta_s \\ I_n(x, y) = E_n(x, y) \cdot c(x, y) \cdot \cos\theta_n \end{cases} \qquad (5)$$

Here, $E_e(x,y)$, $E_w(x,y)$, $E_s(x,y)$, $E_n(x,y)$ are irradiances of the surface element P(x,y) under four different lighting sources separately, and can be calculated by Eqn.3; $\cos\theta_e$, $\cos\theta_w$, $\cos\theta_s$, $\cos\theta_n$ are calculated by Eqn.2.

$$\begin{cases} \cos\theta_e = \frac{\sin\alpha + \cos\alpha \cdot p}{\sqrt{p^2 + q^2 + 1}} \\ \cos\theta_w = \frac{\sin\alpha - \cos\alpha \cdot p}{\sqrt{p^2 + q^2 + 1}} \\ \cos\theta_s = \frac{\sin\alpha - \cos\alpha \cdot q}{\sqrt{p^2 + q^2 + 1}} \\ \cos\theta_n = \frac{\sin\alpha + \cos\alpha \cdot q}{\sqrt{p^2 + q^2 + 1}} \end{cases} \qquad (6)$$

From the above equations, the surface normal gradients p, q and c(x,y) are derived by cross multiplications and transpositions.

$$\begin{cases} p = \frac{I_e E_w - I_w E_e}{I_e E_w + I_w E_e} \cdot \operatorname{tg}\alpha \\ q = \frac{I_n E_s - I_s E_n}{I_n E_s + I_s E_n} \cdot \operatorname{tg}\alpha \\ c = \frac{I_e \cdot \sqrt{p^2 + q^2 + 1}}{\sin\alpha + \cos\alpha \cdot p} \end{cases} \qquad (7)$$

The final step for generating the actual surface (see FIG. 4) is the conversion from surface normal to depth information. That is, for every (x, y) point and normal vector N at (x, y), a z value with respect to the image plane must be computed.

Thus, in FIG. 4, it can be assumed that each of the surface normal $N_0, N_1, N_2, N_3$ is known at the points (0,0), (1,0), (0,1), (1,1), respectively. Starting z value at point (0,0) is either chosen or known. To compute z values at the remaining three points, a function must be chosen to specify how the normal varies along the edges of the patch.

If the points (0,0) and (1,0) are very close relative to surface size, the curve between these points is approximated by its average tangent line. When considering the distance between pixels, this condition holds.

Given the following normal vectors:

$N_0 = (n_{0x}, n_{0y}, n_{0z})$ at (0,0)

$N_1 = (n_{1x}, n_{1y}, n_{1z})$ at (1,0)

$N_2 = (n_{2x}, n_{2y}, n_{2z})$ at (0,1)

$N_3 = (n_{3x}, n_{3y}, n_{3z})$ at (1,1)

It is necessary to compute z at (1,0) which is along the x-axis from (0,0). A desired tangent line passes through the point (0,0,z) and is perpendicular to the average normal between these points. This line can be expressed as $$ax + b(z(1,0) - z(0,0)) = 0 \qquad (8)$$

Where $a = (n_{0x} + n_{1x})/2$ $b = (n_{0z} + n_{1z})/2$

This gives $$z(1,0) = z(0,0) - x(a/b) \text{ with } x=1 \qquad (9)$$

Similarly, approximation along the y axis to find z at (0,1) gives $$z(0,1) = z(0,0) - y(a/b) \text{ with } y=1 \qquad (10)$$

Here $a = (n_{0y} + n_{1y})/2$ $b = (n_{0z} + n_{1z})/2$

To arrive at z(1,1), two values are computed. One value z1(1,1) is arrived at by going from (1,0) to (1,1) in the y direction; the second value z(1,1) is arrived at by going from (0,1) to (1,1) along the x direction. The two values are averaged to give z(1,1):

$$z(1,1) = (z1(1,1) - z2(1,1))/2 \qquad (11)$$

z values can also be computed going along the negative x and y direction if a−1 is substituted for x and y in Eqn.(2) and (3), respectively. This is useful if the value of z at (1,1) is known and the z values at other three points are to be computed.

An algorithm for depth conversion is derived by first choosing an arbitrary z value for a point in the center of the image. Next, z values are determined at all points along the x and y axis passing through this center point shown in FIG. 5a. Finally, z values are computed for the remaining points in each quadrant in the order shown in FIG. 5b. The reconstructed 3-D image of fabric specimen (Grade 1) is shown in FIG. 6.

The apparatus for carrying out the method is shown in FIG. 9 and includes a color digital camera, a lighting box, a frame grabber, and a personal computer. The resolution of digital camera is 1600 pixel×1200 pixel, parallel lighting is controlled in four directions in the lighting box, and the image analysis software is installed in the personal computer.

Twenty fabrics specimens were made from three kinds of woven fabrics with different texture, color and patterns. Each fabric specimens was cut into 180 mm×180 mm, and prepared with varying grades of wrinkling by adjusting washing conditions, pressing pressure and ironing time of the specimens.

Four images of each sample were separately captured at a resolution of 640×480 pixels under the influence of each of the different illuminating beams from the four directions, each of images were cropped into 300×300 pixels for easier processing. Each pixel was assigned a grey-level value from 0 for black to 255 for white.

It was supposed that one surface element is flat, so that its normal vector is taken as (0,0, −1). Considering the surface element of a wrinkling part in the fabric surface, its absolute value of p, q will be larger than other regions. The distributions of p of different fabric wrinkling grades are shown in FIG. 7.

P and Q were used to describe the wrinkling status of fabrics, where $$P = \frac{1}{N}\sum_i^N |p(i)|$$

$$Q = \frac{1}{N}\sum_i^N |q(i)|$$

Here, p(i), q(i) are the first partial derivatives of z with respect to x and y of surface element i, and N is the number of surface elements (pixels) of each image. P describes he wrinkling in the x direction, while Q describes the wrinkling in the y direction. P+Q is used to describe the wrinkling of whole fabric surface.

In order to make the rating generated by this described image analysis system consistent with the visual standards, all the samples were first evaluated by experienced judges according to the AATCC standards, and the correlation between objective and subjective measurement carried out on the basis of the derived wrinkling features and the subjective grades.

Table 2 below shows the results of objective measurements and subjective evaluation. Sample A, B, C are different in patterns, colors and textures, and the subjective grade of each specimen is the average of five experienced judges' evaluation. In the table, P of B1 is higher than B2, but P+Q of B1 is lower than B2, so it is clear that it is better to describe fabric wrinkling of whole surface using P+Q rather than using P or Q.

| Fabric Code | | P + Q | P | Q | Subjective Grade |
|---|---|---|---|---|---|
| Sample A | A1 | 0.035971 | 0.020097 | 0.015874 | 5 |
| | A2 | 0.041352 | 0.022775 | 0.018577 | 3.6 |
| | A3 | 0.044955 | 0.024703 | 0.020252 | 3 |
| | A4 | 0.059857 | 0.035655 | 0.024202 | 2.1 |
| | A5 | 0.058622 | 0.02739 | 0.031232 | 2.4 |
| | A6 | 0.07285 | 0.037493 | 0.035357 | 1.5 |
| | A7 | 0.083917 | 0.039108 | 0.044809 | 1.1 |
| Sample B | B1 | 0.024463 | 0.012993 | 0.01147 | 5 |
| | B2 | 0.024621 | 0.011665 | 0.012956 | 4.2 |
| | B3 | 0.028088 | 0.012697 | 0.015391 | 4.1 |
| | B4 | 0.038737 | 0.018134 | 0.020603 | 2.2 |
| | B5 | 0.046813 | 0.03229 | 0.014523 | 1.6 |
| | B6 | 0.03927 | 0.021026 | 0.018244 | 2.9 |
| | B7 | 0.054992 | 0.03274 | 0.022252 | 1 |

Grade 1(Serious Wrinkling) Grade 5(No Wrinkling)

From FIG. 8, it will be noted that the correlation coefficient between P+Q and the subjective wrinkling grade is very high, sample A is 0.9764, sample B is 0.9616, and sample C is 0.8365. According to this result, the objective method provided by this invention measures fabric wrinkling effectively.

Thus, the described photometric stereo method evaluates fabric wrinkling by extracting the 3D surface information and enables a calibrated uses feature P+Q to give an objective 'description' of the fabric wrinkling. The method can be applied to fabrics with coloured or physical patterns. From four camera images to provide different illuminating directions, an effective feature P+Q of the 3D images is used to describe fabric wrinkling. The results indicate that photometric stereo can be used for analysis of the fabric surface instead of the common image analysis techniques, even for fabrics with patterns and different colors.

It will be appreciated that for measurements and evaluations of appearance the method and apparatus may be used for deriving the various described parameters by analysis of reflections of separate images captured by the camera. Although four light beams are preferred in carrying out the invention, it is possible to use only two light beam for some applications.

We claim:

1. A method of three-dimensional measurement, evaluation, and grading of fabric/textile structure/garment appearance using a photometric stereo technique, the method comprising:

with a fixed digital camera positioned above a piece of fabric, shining parallel light beams from at least two different inclined directions onto a surface of the fabric, capturing with the camera different reflected images of the surface of the fabric while the surface of the fabric is illuminated from each of the at least two different inclined directions, and analysing the reflected images captured to derive surface normal gradients of the fabric based on intensities of light reflected from a number of evenly distributed points on the surface.

2. The method according to claim 1, including shining parallel light beams onto the surface of the fabric from four different directions.

3. An apparatus for three dimensional measurement, evaluation, and grading of fabric/textile structure/garment appearance using a photometric stereo technique, the apparatus including:

a digital camera mounted above a piece of fabric, means to illuminate the fabric from at least two different directions using calibrated inclined parallel light sources integrated in one housing, wherein different images of the fabric, illuminated from the at least two different directions, are captured by the camera, means for analysing images of the fabric captured by the camera, and a computer programmed to derive values of P and Q from the images captured, where P and Q are summations of surface normal gradients for a plurality of evenly distributed points in an x direction and in a y direction, respectively, on the surface of the fabric.

4. A method of grading fabric/textile structure appearance based on values P and Q, the method comprising:

using a fixed digital camera positioned above a piece of the fabric, shining at least two different parallel light beams from inclined directions onto a the surface of the fabric, capturing different images reflected from the surface with the camera, analysing the images captured to derive values of P and Q, where P and Q are summations of surface gradients for a plurality of evenly distributed points in an x direction and in a y direction, respectively, calibrating P+Q against a subjective grade analysis of the fabric, and thereafter, using calibrated P and Q and determining the grade of the fabric.

5. The method of claim 4, including using four different parallel light beams.

6. The method of claim 4, in which the surface gradients p and q are derived from $$p = \frac{I_e E_w - I_w E_e}{I_e E_w + I_w E_e} \cdot tg\alpha$$

$$q = \frac{I_n E_s - I_s E_n}{I_n E_s + I_s E_n} \cdot tg\alpha$$

$$c = \frac{I_e \cdot \sqrt{p^2 + q^2 + 1}}{\sin\alpha + \cos\alpha \cdot p}.$$

7. An apparatus for three dimensional measurement, evaluation, and grading of fabric/textile structure/garment appearance using a photometric stereo technique including:

a digital camera mounted above a piece of fabric, means to separately shine inclined parallel beams from at least two different directions onto a surface of the fabric below the camera, means for analysing separate images of the fabric, illuminated from the at least two different inclined directions, captured by the camera for each light beam, respectively, and a computer programmed to derive surface normal gradients of the fabric based on intensities of light reflected from a number of evenly distributed points on the surface.

8. An apparatus for three-dimensional measurement, evaluation, and grading of fabric/textile structure/garment appearance using a photometric stereo technique according to claim 7, including means for shining inclined parallel light beams from four different directions evenly distributed with respect to the camera.

* * * * *